United States Patent
Blacklidge

(10) Patent No.: US 9,101,421 B2
(45) Date of Patent: Aug. 11, 2015

(54) METATARSAL FIXATION DEVICE, SYSTEM AND METHOD

(71) Applicant: Solana Surgical, LLC, Memphis, TN (US)

(72) Inventor: Douglas K. Blacklidge, Kokomo, IN (US)

(73) Assignee: Solana Surgical, LLC, Memphis, TN (US)

( * ) Notice: Subject to any disclaimer, the term of this patent is extended or adjusted under 35 U.S.C. 154(b) by 86 days.

(21) Appl. No.: 13/653,600

(22) Filed: Oct. 17, 2012

(65) Prior Publication Data

US 2013/0150853 A1 Jun. 13, 2013

Related U.S. Application Data

(60) Provisional application No. 61/569,605, filed on Dec. 12, 2011.

(51) Int. Cl.
*A61B 17/80* (2006.01)

(52) U.S. Cl.
CPC ........... *A61B 17/8004* (2013.01); *A61B 17/809* (2013.01); *A61B 17/8052* (2013.01); *A61B 17/8057* (2013.01); *A61B 17/8061* (2013.01); *A61B 17/8085* (2013.01)

(58) Field of Classification Search
CPC ........... A61B 17/8004; A61B 17/8052; A61B 17/8057; A61B 17/8061; A61B 17/8085; A61B 17/809
USPC ........ 606/86 B, 280–286, 297–299, 902, 906
See application file for complete search history.

(56) References Cited

U.S. PATENT DOCUMENTS

| | | | |
|---|---|---|---|
| 4,651,724 A | 3/1987 | Berentey et al. | |
| 5,674,222 A | 10/1997 | Berger et al. | |
| 6,283,969 B1 | 9/2001 | Grusin et al. | |
| 6,730,090 B2 | 5/2004 | Orbay et al. | |
| 7,229,444 B2 | 6/2007 | Boyd | |
| 7,335,204 B2 * | 2/2008 | Tornier | 606/284 |
| 8,603,148 B2 * | 12/2013 | Raven et al. | 606/286 |
| 8,906,070 B2 * | 12/2014 | Medoff | 606/280 |
| 2008/0119895 A1 * | 5/2008 | Manceau | 606/280 |
| 2009/0198277 A1 | 8/2009 | Gordon et al. | |
| 2010/0069966 A1 | 3/2010 | Castaneda et al. | |
| 2011/0029025 A1 | 2/2011 | Medoff | |

FOREIGN PATENT DOCUMENTS

| | | | | |
|---|---|---|---|---|
| JP | 03012145 A | * | 1/1991 | ............. A61B 17/58 |
| WO | WO 2009086402 A1 | * | 7/2009 | ............. A61B 17/80 |

* cited by examiner

*Primary Examiner* — Larry E Waggle, Jr.
(74) *Attorney, Agent, or Firm* — Duane Morris LLP

(57) ABSTRACT

A metatarsal fixation device is provided for fixation of osteotomy or fracture of a distal metatarsal metaphysis bone of the human foot and for fixation of an associated capsule to the metatarsal head. The device includes a metallic bone plate with a series of screw holes along an elongated portion of the plate and a combination of a singular screw hole and a resilient clamp on an end of the elongated portion. The resilient clamp has two arched resilient arms extending laterally outward from an end of the elongated portion. Each arm has a plurality of spikes on an inner surface thereof providing points of contact that compress and attach a metatarsal phalangeal joint capsule portion to the medial and/or lateral aspect of the metatarsal head, thereby facilitating realignment of the metatarsophalangeal joint and respective digit. The resilient arms are biased to grasp lateral sides of a metatarsal head and any associated capsule portion.

16 Claims, 11 Drawing Sheets

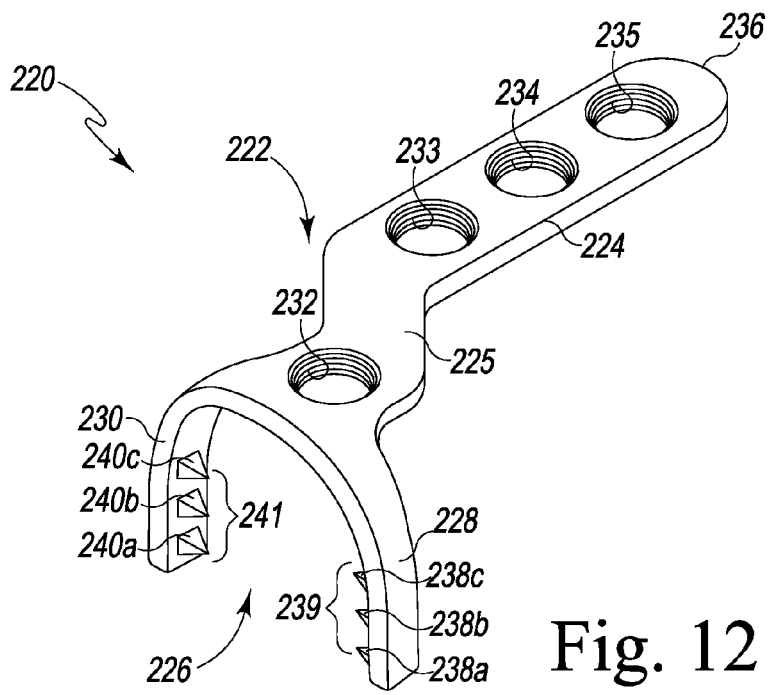
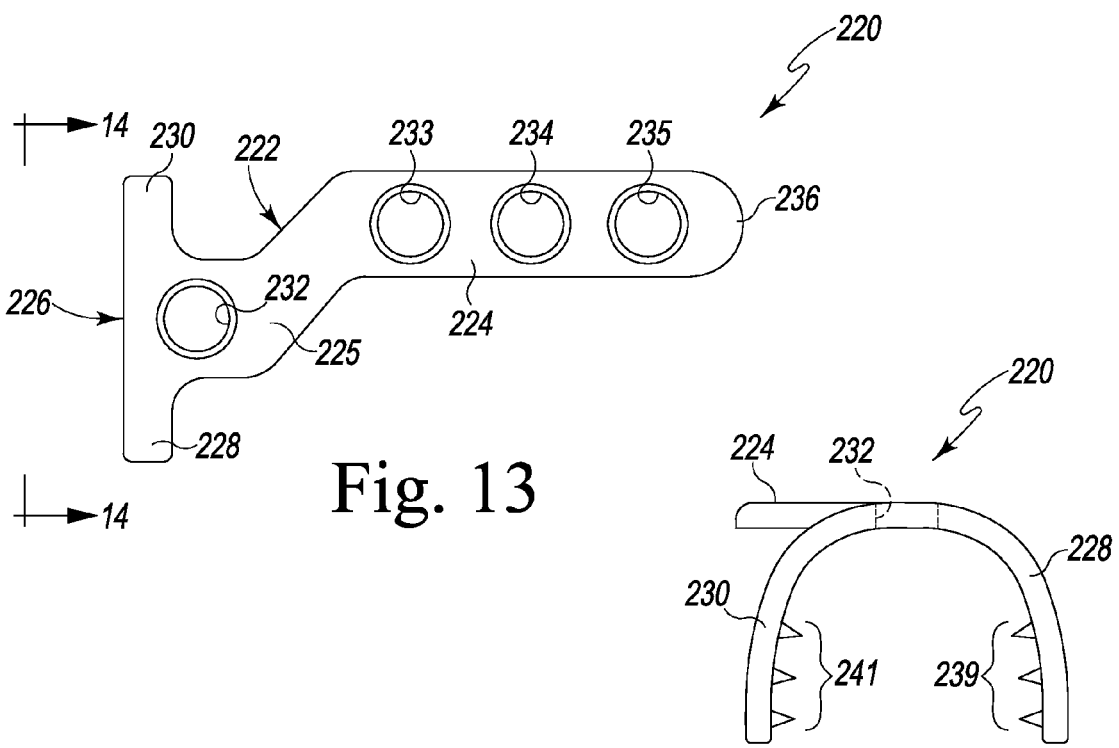

METATARSAL FIXATION DEVICE, SYSTEM AND METHOD

RELATED APPLICATIONS

This patent application claims the benefit of and/or priority under 35 U.S.C. §119(e) to U.S. Provisional Patent Application Ser. No. 61/569,605 filed Dec. 12, 2011, entitled "Metatarsal Bone Fixation Device, System and Method" the entire contents of which is specifically incorporated herein by this reference.

BACKGROUND OF THE INVENTION

1. Field of the Invention

The present invention relates to surgically implanted devices for fixation of human bones and associated tissue, and particularly to surgically implanted devices for fixation of metatarsal bones and associated tissue. More particularly, the present invention relates to surgically implanted devices for internal fixation of a distal portion of a metatarsal bone with a metatarsal diaphysis along with any capsular corrections.

2. Background

The distal metatarsal metaphysis of the human foot is a very common site of fracture as well as repositional osteotomy for correction of deformities as well as other reasons. Osteotomy to provide shortening of a metatarsal is commonly performed to decrease plantar forefoot pressure at the site of a metatarsal head. Shortening osteotomy is most commonly performed on central metatarsals. Shortening the metatarsal shortens the lever and decreases the pressure at the plantar forefoot generated during the propulsive phase of gait. Shortening osteotomy can alleviate pain caused by excessive pressure due to a relatively long metatarsal. Shortening osteotomy can also help heal plantar skin keratosis or ulceration due to excessive pressure. Shortening osteotomy is often performed in combination with hammertoe corrective procedures.

Stable fixation of the metatarsal head fragment to the diaphysis (shaft) of the metatarsal in order to provide appropriate correction and ideal anatomic osteotomy location can be challenging and inadequate with current devices available. Osteotomy orientation has currently evolved to facilitate fixation while sacrificing ideal correction and ideal osteotomy anatomic location. A pure segmental shortening osteotomy performed at the distal metaphysis is ideal but very difficult to fixate. The distal fragment is small and current fixation devices do not adequately fixate this fragment in order to stabilize the metaphyseal osteotomy.

To address this problem, currently a more proximal segmental shortening osteotomy is performed so a dorsal plate can be used with at least two screws to engage the distal fragment. Plates are available with both non-locking and locking screws to engage the bone. This more proximal osteotomy results in diaphyseal bone shortening. Metaphyseal bone has a greater healing potential than diaphyseal bone and is therefore the preferable location for osteotomy. Furthermore, the more proximal osteotomy is potentially stressed by a longer lever distal to the osteotomy.

The most common osteotomy for shortening of the central metatarsals is a long oblique osteotomy from distal dorsal to proximal plantar. This is partially a metaphyseal osteotomy and facilitates fixation from dorsal to plantar with isolated screws or pins. The osteotomy orientation unfortunately often results in plantar displacement of the distal fragment with the shortening. The distal dorsal cortical spike is also subject to fracture at the fixation site which can result in displacement of the osteotomy.

Osteotomies to displace a metatarsal head laterally or medially are often performed to correct bone prominence of the first (hallux abducto valgus/bunion deformity) or fifth metatarsal (tailor's bunion/bunionette deformity) in the transverse plane of the foot. Fixation of the metatarsal head fragment to the shaft fragment is again facilitated by osteotomy orientation. Osteotomy configurations include: oblique, chevron, chevron with longer arm dorsal or plantar, "Z"/scarf and others. Current internal fixation options include: k-wires, screws, plates, wire, staples. These osteotomies are all subject to displacement with current fixation options as the distal fragment is difficult to secure with current devices. The aging population and associated decrease in bone density further increases the potential loss of fixation with current techniques and devices. The problem continues to be inadequate stabilization of an osteotomy due to suboptimal fixation of the metatarsal head fragment.

Moreover, often associated with metatarsal deformities are respective digital deformities. Mal-alignment in the transverse plane includes digits deviated medially or laterally from their proper position. When metatarsal realignment osteotomies are performed, capsular corrections must also be included for realignment of the respective digit. The capsular corrections include releasing or lengthening the tight soft tissue preventing realignment and tightening the capsule/ligament on the side where it is lax. Tightening of the capsule is performed by removing a section or advancing the lax capsule from its original attachment and reattaching. The standard means of securing is sutures. Capsule tightening is difficult when adjacent structures prevent access to the site of repair. Also, suture repair requires exposure. The central metatarsophalangeal joints are particularly difficult to perform capsular balancing due to the adjacent joints medial and lateral restricting exposure.

It is therefore evident from the above that there is a need for a system, device and method for better fixation of a metatarsal osteotomy or fracture.

It is further evident from the above that there is a need for better internal fixation of a distal portion of a metatarsal bone and a diaphysis of the metatarsal bone so as to stabilize an osteotomy or fracture of the metatarsal distal metaphysis.

It is moreover evident from the above that there is a need for a system, device and method for fixation of ligamentous and joint capsular tissue to a metatarsal head particularly in connection with fixation of a metatarsal metaphyseal osteotomy or fracture.

SUMMARY OF THE INVENTION

A bone structure fixation device, system and method of use is provided for fixation of bones of the foot and hand along with tissue component correction particularly, but not necessarily, for internal fixation of a distal portion of metatarsal bone (e.g. an epiphysis thereof or a metaphysis and epiphysis thereof) with an associated diaphysis (i.e. shaft) of the metatarsal bone so as to stabilize an osteotomy or fracture of the metatarsal bone, and for internal fixation of ligamentous and/or joint capsular tissue performed in connection with the osteotomy or fracture.

The present invention provides better fixation between a distal portion of a metatarsal bone and its diaphysis in the event of a metaphyseal osteotomy or fracture, and/or the need to provide capsular corrections, including releasing or lengthening the tight soft tissue preventing realignment and tightening the capsule/ligament on the side where it is lax. The present metatarsal fixation device therefore provides stable fixation of the diaphyseal segment—with plate and locking screw technology, and the metatarsal head fragment via clamping technology, with the clamping technology also providing joint soft tissue/capsule/ligament/capsular realignment and/or tightening (correction).

In broad terms, the present metatarsal fixation device comprises a metallic bone fixation plate having a series of threaded locking screw holes along an elongated portion of the plate and a combination of a threaded locking screw hole and a resilient clamp on an end of the elongated portion, the resilient clamp characterized by resilient arched, spiked arms extending transverse to the end of the elongated portion. The resilient or spring-like arched, spiked arms have a natural curvature sized and designed to grasp onto an epiphysis of a metatarsal bone and associated capsule portion or capsular tissue after the arms have been resiliently expanded by an expansion force. After expansion, the resilient, spring-like arms return to a pre-expansion state in order to clamp, clasp and/or grasp onto the epiphysis (metatarsal head) at the medial and lateral sides thereof and a capsule/ligament portion. The metatarsal fixation device thus provides stability to a small, potentially unstable metatarsal head fragment as well as providing capsular/ligament fixation.

The space between the three diaphyseal screws (i.e. along the elongated portion of the plate) and the distal screw (i.e. proximate the clamp), with medial and lateral arms, can be the site of an osteotomy for segmental shortening, displacement osteotomy, or fracture. This metaphyseal site of bone healing is protected from potentially healing-disruptive stresses by this invention. The spiked arms provide fixation of any capsular/ligament correction to the epiphysis.

In a particular form, a metatarsal fixation device is defined by a generally rigid metallic plate having an elongated portion with circular threaded holes spaced therealong to receive threaded bone screws. The threaded holes are preferably, but not necessarily, evenly spaced along the elongated portion beginning at one end thereof. A clasp and a singular circular threaded hole are provided at an opposite end of the elongated portion. The clasp is defined by two arms that project from each side of the elongated portion end and 180° from each other. Each arm is curved, arched or arced to create a general "U" shape and/or has a curvature that mimics a curvature of an epiphysis. The arms preferably, but not necessarily, project in the same direction as the bone screws. In this manner, the shape of the elongated portion and clasp (i.e. the plate) is nearly anatomically congruous to the metatarsal. The end of each arm incorporates spikes to engage the metatarsal head and capsule/ligament medially and laterally.

The spikes on each arm's interior serve as a point of fixation for the capsule advancement if the arms are used extra capsularly. The side of the metatarsophalangeal joint in need of capsular tightening may have the capsule released from the native attachment to the metatarsal head. The capsule is then pulled proximally to pull the digit into proper alignment. The present plate is applied extracapsularly and the arms providing compression, securing the advanced capsule back to the metatarsal head with the digit in proper alignment. Minimal exposure is required between the capsule and adjacent soft tissues to insert the fixation plate's arm and the implant instrument.

The implant instrument comprises pliers specifically designed to expand the arms about the medial and lateral aspects of the metatarsal head then release the arms causing the spikes to clamp, grasp of clasp onto and/or into the medial and lateral aspect of the metatarsal head and any ligamentous/ capsule tissue. The plate arms with their associated spikes along with the isolated screw engage the metatarsal head bone fragment while the three opposite end screw holes of the elongated portion and its screws engage the metatarsal diaphysis. The space between the isolated screw hole and the series of three screw holes spans the metatarsal metaphyseal osteotomy or fracture site.

The present fixation device serves two purposes. One purpose is the fixation of the metatarsal metaphyseal osteotomy or fracture. The other purpose is the fixation of the capsule to the metatarsal head.

While the present invention is applicable to other bone structures, the present fixation device is described with reference to metatarsal bones, it being understood that the present fixation device may be used for other bones and/or bone structures of the body.

Further aspects of the present invention will become apparent from consideration of the drawings and the following description of preferred embodiments of the invention. A person skilled in the art will realize that other embodiments of the invention are possible and that the details of the invention can be modified in a number of respects without departing from the inventive concept. The following drawings and description are to be regarded as illustrative in nature and not restrictive.

BRIEF DESCRIPTION OF THE DRAWINGS

The features of the invention will be better understood by reference to the accompanying drawings which illustrate presently preferred embodiments of the invention, wherein:

FIG. 12 is an oblique of another embodiment of a metatarsal bone fixation device fashioned in accordance with the present principles wherein an attachment portion of the device is angled or offset relative to a longitudinal axis of a plate of the device;

FIG. 13 is a top view of the metatarsal bone fixation device of FIG. 12;

FIG. 14 is a front view of the metatarsal bone fixation device of FIG. 12 taken along line 12-12 of FIG. 13;

DETAILED DESCRIPTION OF THE INVENTION

Figure 1:
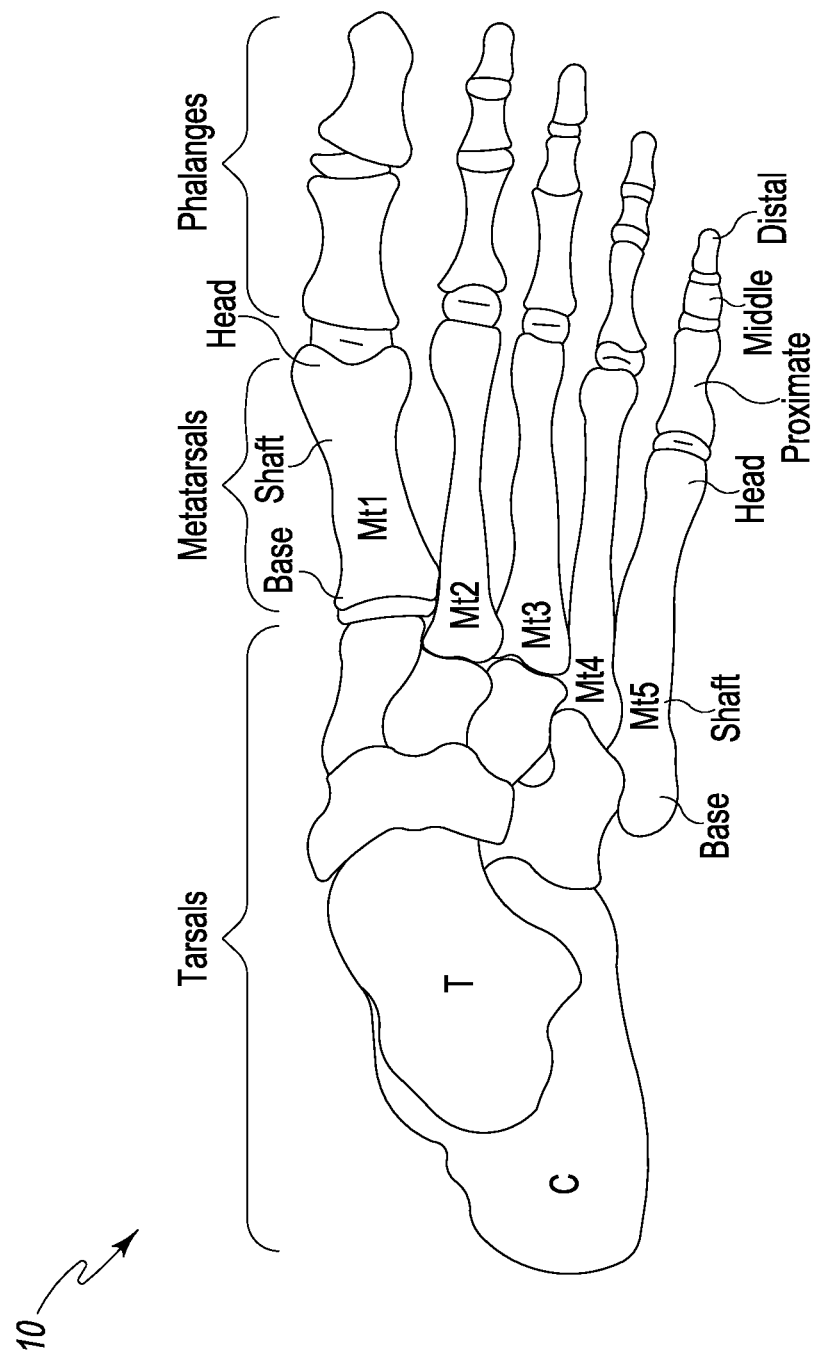
FIG. 1 is a top view of bones of a human foot particularly showing the tarsals, metatarsals and phalanges thereof.
Figure 2:
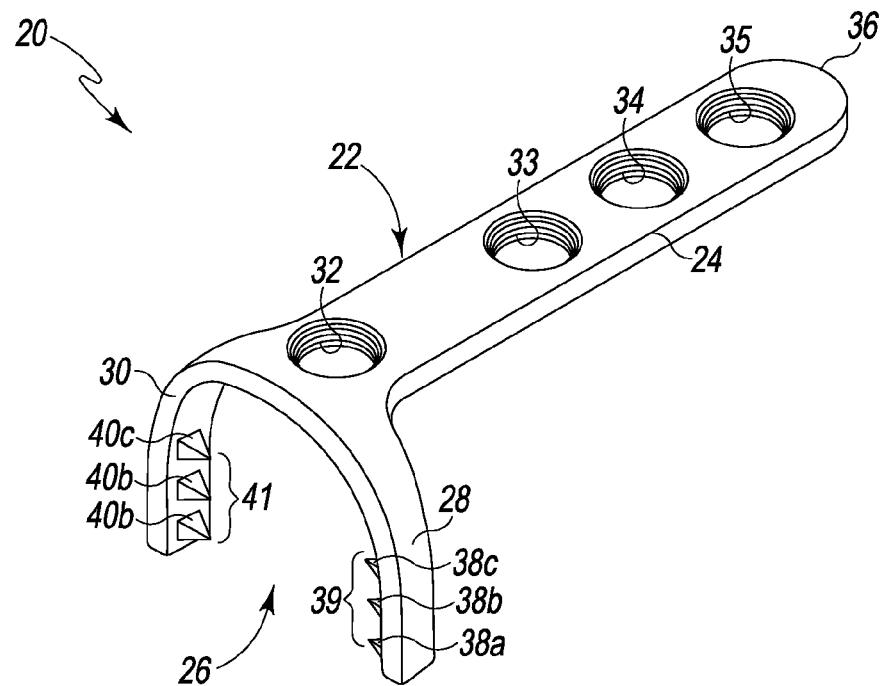
FIG. 2 is an oblique view of an embodiment of a metatarsal fixation device fashioned in accordance with the present principles.
Figure 3:
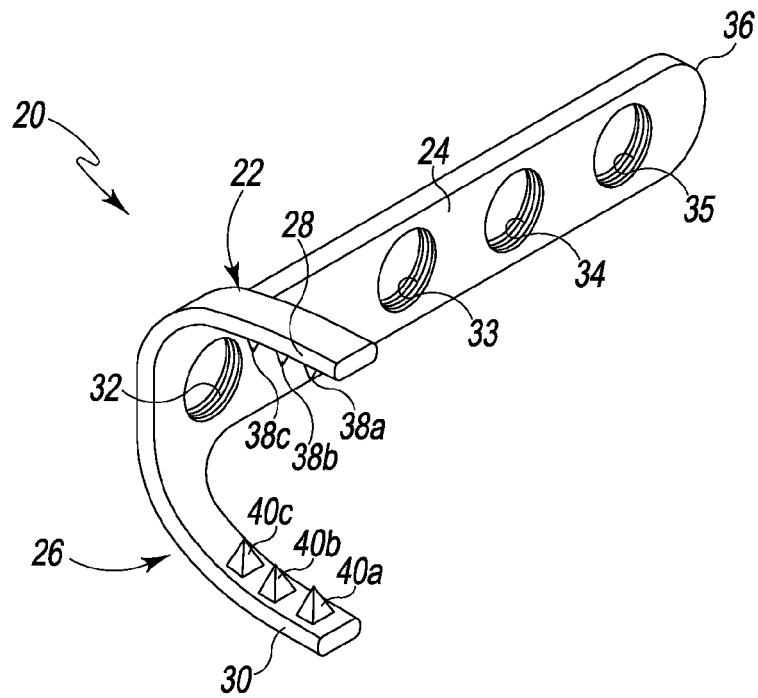
FIG. 3 is a side oblique view of the metatarsal bone fixation device of FIG. 2.

Referring to FIG. 1, there is depicted for purposes of illustration a diagram of the general bones of a human foot 10 particularly a right human foot as seen viewed the top. The human foot has tarsal bones or tarsals including the calcaneous C and the talus T, the metatarsal bones or metatarsals and phalange bones or phalanges. There are generally five metatarsals (M1, M2, M3, M4 and M5) each having a base, shaft and head, and generally five phalanges each having a proximate, middle and distal portion. While the present bone fixation device may be used for various bones of the body, it is especially configured for the fixation of a metatarsal. It is thus with respect to a metatarsal that the present invention will be described.

Figure 8:
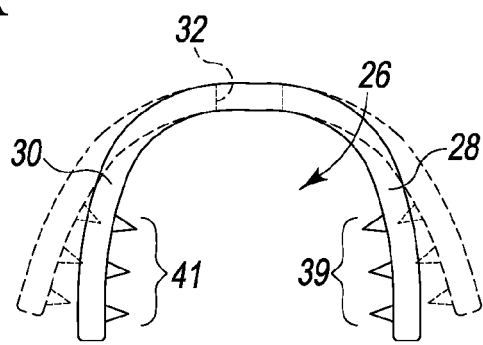
FIG. 8 is a front view of the metatarsal bone fixation device of FIG. 2 illustrating the manner in which the metatarsal bone fixation device flexes for attachment to a metatarsal head or to the metatarsal head and the metatarsal phalangeal joint capsule to the medial or lateral aspect of the metatarsal head.

Referring now to FIGS. 1-8, there is depicted several views of a bone fixation device generally designated 20. As indicated, the bone fixation device 20 is particularly suited for and is thus fashioned as a metatarsal fixation device 20. It should be appreciated however, that the metatarsal fixation device 20 and/or its principles are applicable to other bones of the foot as well as to bones of the hand. The metatarsal bone fixation device 20 is characterized by a plate 22 having an elongated portion 24 and a clamping portion 26. The clamping portion or clamp 26 is characterized by arms 28 and 30 that extend from lateral or transverse sides of a distal end (as implanted) of the elongated portion 24. FIG. 8 illustrates the resilient properties of the clamping portion 26 that allow the clamping portion 26 to naturally compress against a metatarsal head. As seen, the arms 28, 30 initially extend transverse to the distal end of the elongated portion 24 then curve or arch downward and away from the end of the elongated portion 24 to generally form a U shape.

The plate 22 is composed of a generally rigid but resilient, biocompatible metal that is preferably, but not necessarily, approximately 1 mm thick. The underside of the plate 22 or the surface of the plate 22 that contacts the bone surface may include a slight radius from medial to lateral to match the contour of the bone such as discerned in FIG. 4A.

The elongated portion 24 of the plate 22 has an anchoring section fashioned as a plurality of threaded holes (holes 33, 34, 35) that extend along the longitudinal length of the elongated portion 24 from a proximate end 36 thereof towards a distal end thereof (i.e. the clamping portion 26). It should be appreciated that the anchoring section may include more or less threaded holes with three threaded holes being preferred. The three threaded holes 33, 34, 35 are depicted at one end of the elongated portion 24 arranged in linear orientation and evenly spaced. Other configurations, however, may be used and are contemplated.

Figure 4:
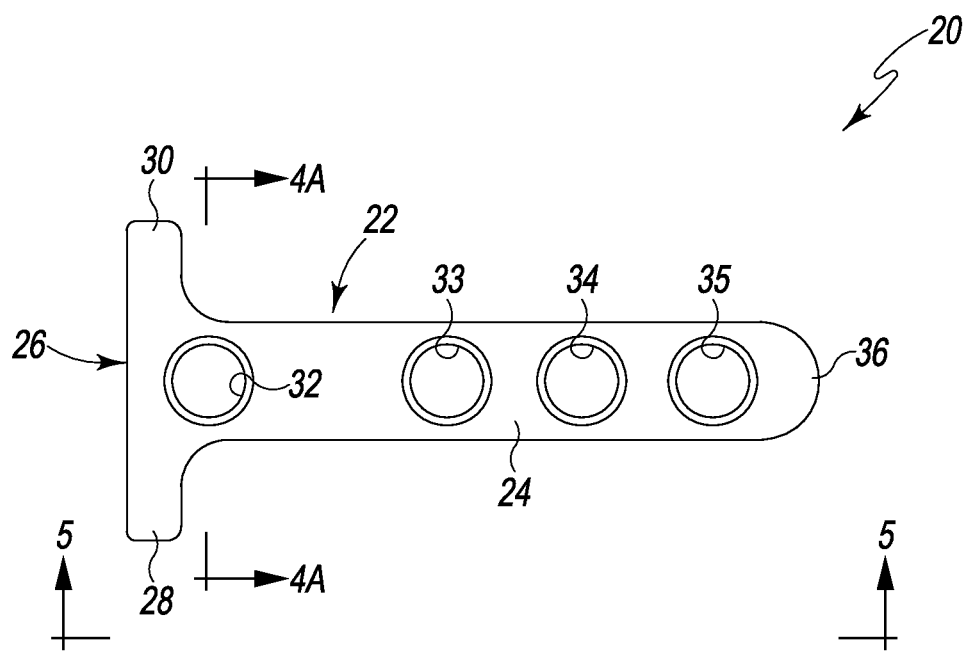
FIG. 4 is a top plan view of the metatarsal bone fixation device of FIG. 2.
Figure 4A:
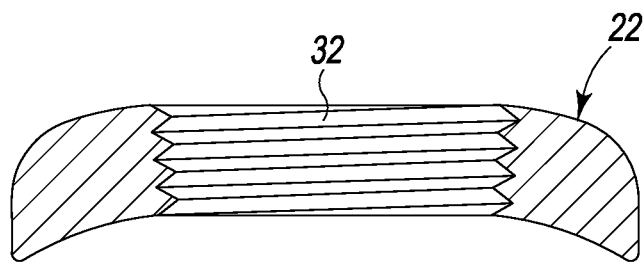
FIG. 4A is a sectional view of the metatarsal bone fixation device of FIG. 2 taken along line 4A-4A of FIG. 4.
Figure 5:
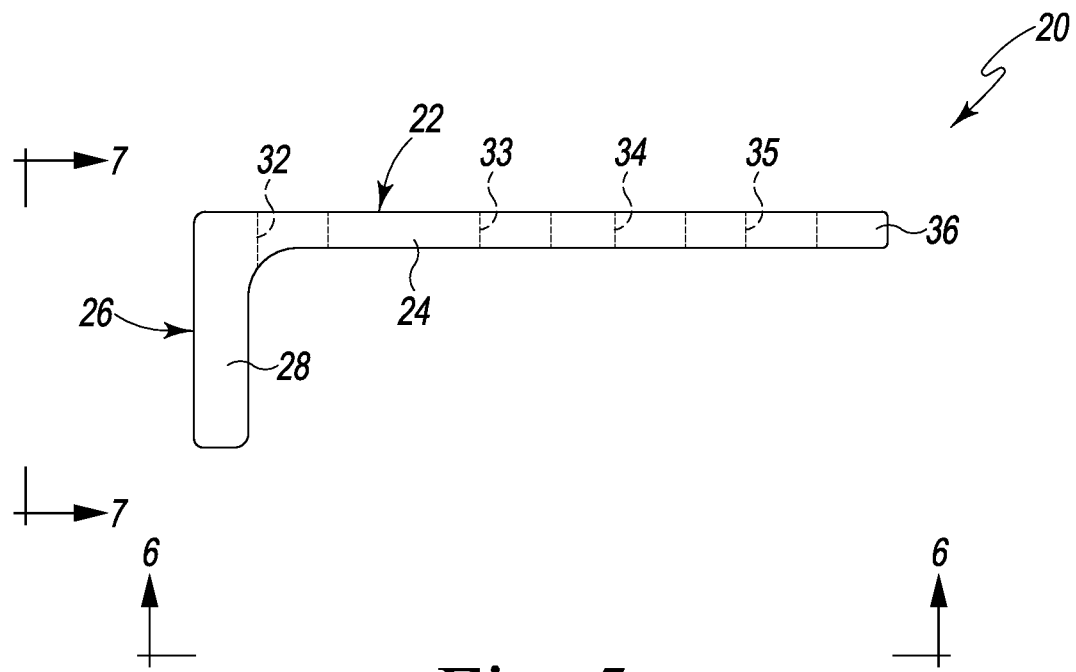
FIG. 5 is a side view of the metatarsal bone fixation device of FIG. 2 taken along line 5-5 of FIG. 4.
Figure 6:
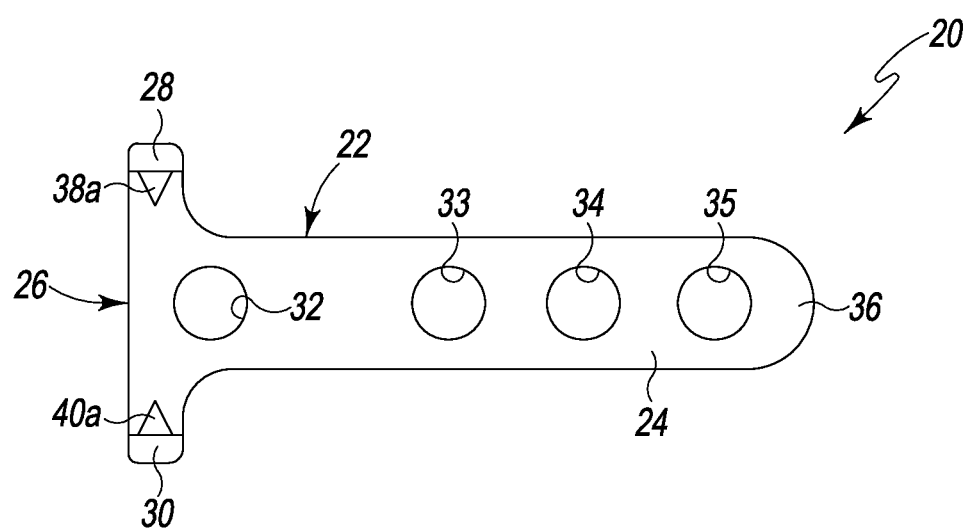
FIG. 6 is a bottom view of the metatarsal bone fixation device of FIG. 2 taken along line 6-6 of FIG. 5.
Figure 7:
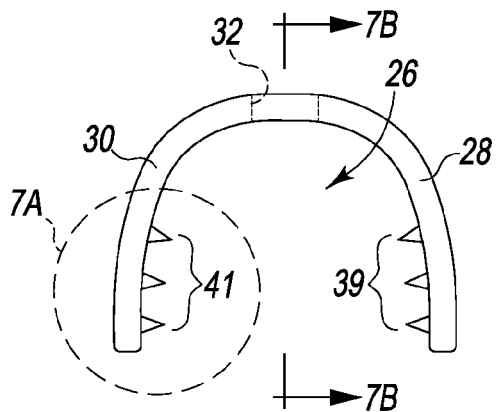
FIG. 7 is a front view of the metatarsal bone fixation device of FIG. 2 taken along line 7-7 of FIG. 5.
Figure 7A:
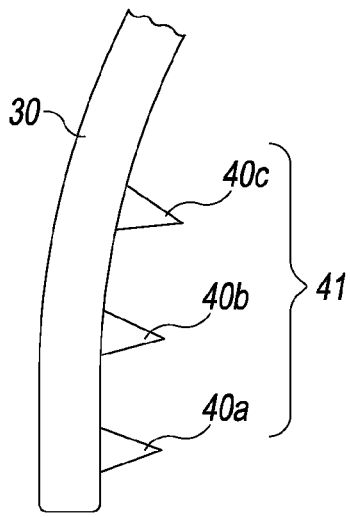
FIG. 7A is an enlarged front view of a portion of the metatarsal bone fixation device of FIG. 2 taken along circle 7A of FIG. 7, particularly showing attachment structures of an arm thereof.
Figure 7B:
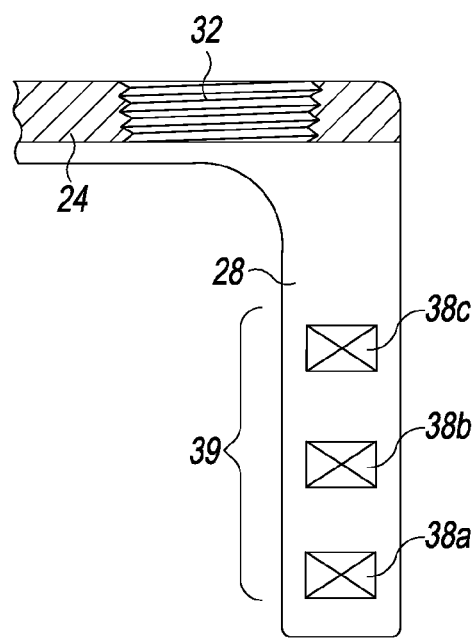
FIG. 7B is an enlarged sectional view of a front portion of the metatarsal fixation device of FIG. 2 taken along line 7B-7B of FIG. 7.
Figure 20:
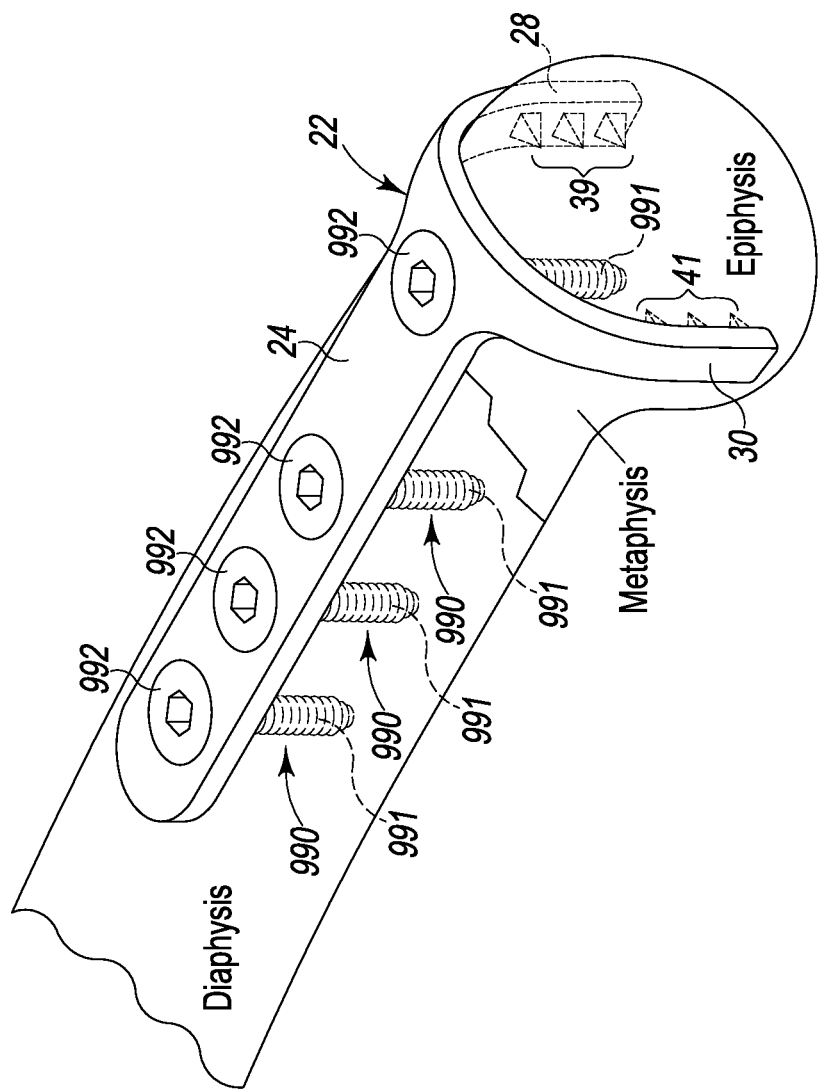
FIG. 20 is an oblique view of the metatarsal bone fixation device of FIG. 1 affixed to a metatarsal and, particularly to a diaphysis and epiphysis of the metatarsal for the stabilization of a metaphyseal fracture thereof, the arms of the attachment portion of the metatarsal bone fixation positioned about and onto the epiphysis, the jagged line representing a fracture/osteotomy.

A single threaded hole 32 is centered at the distal end of the plate 22 at the clamping portion 26. The single or isolated hole 32 is separated from the next hole 33 of the anchoring section by an appropriate distance (which in the case of a metatarsal, is approximately 10 mm). Each of the threaded holes 33, 34, 35, 32 is for receiving threaded bone screws when the device is implanted/attached. This is seen in FIG. 20 where bone screws 990 extend from the holes 32, 33, 34, 35, and into the bone when the device 20 is installed. The bone screws 990 preferably have threaded shafts 991 that extend into and grip the bone. Referring to FIG. 4A, the threaded hole 32 is shown in greater detail as exemplary of all of the threaded holes 32, 33, 34, and 35.

The clamping portion 26 is characterized by two arms 28, 30 that project from lateral sides of the distal end of the elongated plate 24. The arms 28, 30 project transverse from the lateral sides of the distal end of the elongated plate 24 then extend downwardly to generally form a U shape. The arm 28 includes an attachment structure 39 on an inside surface thereof. The attachment structure 39 is defined by a plurality of spikes or spike-like structures 38a, 38b, 38c that project inward from the inside surface of the arm 28. Preferably, but not necessarily, the spikes 38a, 38b, 38c are the same shape and size. In one form, the spikes 38a, 38b, 38c protrude 1 mm from the inner surface of the am 28. It should be appreciated however, that the spikes of the attachment structure 39 may be shaped and sized differently if desired. Also, the spikes 38a, 38b, 38c are preferably, but not necessarily, evenly spaced relative to each other beginning proximate an end of the arm 28 distal the elongated plate 24. The spikes provide points of contact with the metatarsal head affording various points of fixation. The spikes 38a, 38b, 38c are shaped and sized to grasp or clamp against, affix or attach to, a lateral side of a metatarsal head. Additionally, the spikes 38a, 38b, 38c grasp, clamp or compress against a capsule or a capsule portion of the metatarsal joint which then affixes or attaches the capsule or capsule portion of the metatarsal joint to a lateral side of the metatarsal head, thereby facilitating realignment of the metatarsalsophalageal joint and respective digit.

The arm 30 includes an attachment structure 41 on an inside surface thereof in like manner as the attachment structure 39 of the arm 28. The attachment structure 41 is defined by a plurality of spikes or spike-like structures 40a, 40b, 40c that project inward from the inside surface of the arm 30. Preferably, but not necessarily, the spikes 40a, 40b, 40c are the same shape and size. In one form, the spikes 40a, 40b, 40c protrude 1 mm from the inner surface of the arm 30. It should be appreciated however, that the spikes of the attachment structure 41 may be shaped and sized differently if desired. Also, the spikes 40a, 40b, 40c are preferably, but not necessarily, evenly spaced relative to each other beginning proximate an end of the arm 30 distal the elongated plate 24. The spikes provide points of contact with the metatarsal head affording various points of fixation. The spikes 40a, 40b, 40c are shaped and sized to grasp or clamp against, affix or attach to, lateral sides of a metatarsal head. Additionally, the spikes 40a, 40b, 40c grasp, clamp or compress against a capsule or a capsule portion of the metatarsal joint which then affixes or attaches the capsule or capsule portion of the metatarsal joint to a lateral side of the metatarsal head, thereby facilitating realignment of the metatarsalsophalageal joint and respective digit.

The arms 28, 30 are resilient or spring-like such that they return to their original shape after being spread, such as during implantation of the device. Particularly, the resilient arms 28, 30 are configured and shaped to compress, grasp or clamp against or attach to the metatarsal head under their own natural resilient force. As such, the attachment structures 39, 41 (and, particularly the spikes 38, 40 of the attachment structures 39, 41) contact, compress and grasp or clamp onto the metatarsal head with or without clamping or securing of a capsule or capsule portion depending on whether the clamping portion 26 is used extracapsularly (with capsule securing) or intracapsularly (without capsule securing). As illustrated in FIG. 8, the natural clamping position or state of the arms 28, 30 (i.e. clamping portion 26) is represented by the unbroken lines and a temporary expanded position or state of the arms 28, 30 is represented by the broken lines. The arms 28, 30 are expanded during implantation of the device as per an instrument 950 illustrated in FIG. 21 which is described more fully below. In summary, the expanded position is achieved by forcibly spreading the arms 28, 30 as via the instrument 950.

It should be appreciated that the metatarsal fixation device 20 is used where the metatarsal head or epiphysis is attached to the metatarsal diaphysis (bone shaft) along its original longitudinal axis such as shown in FIG. 20 where a fracture of the metaphysis of the metatarsal has been repaired through the use of the metatarsal fixation device 20. In FIG. 20, the capsule and other metatarsal joint tissue is not shown. In cases such as rectification of a deformity, injury or the ramifications of disease where fixation of the epiphysis is intentionally not aligned with the original longitudinal axis of the diaphysis, a modified metatarsal fixation device is used.

Figure 9:
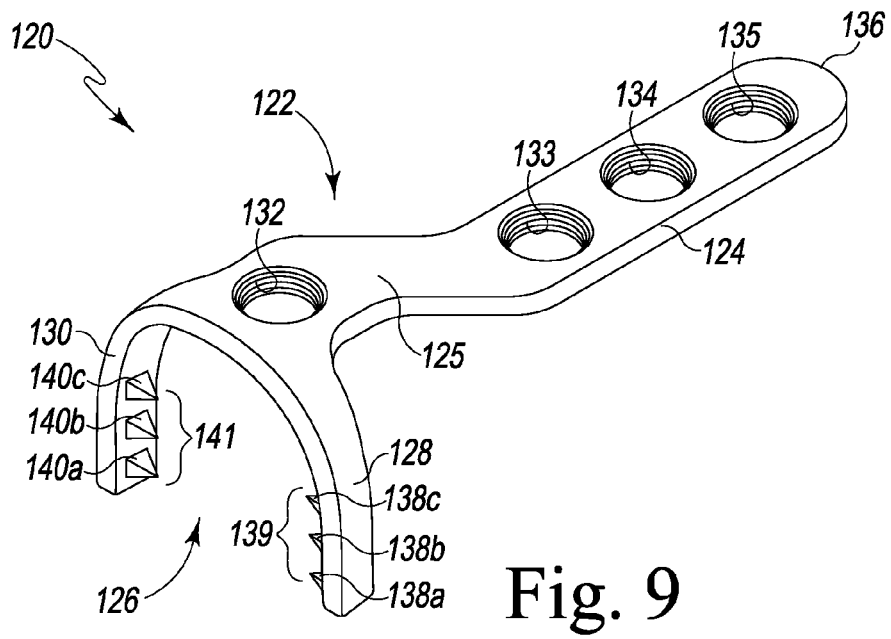
FIG. 9 is an oblique view of another embodiment of a metatarsal bone fixation device fashioned in accordance with the present principles wherein an attachment portion of the device is angled or offset relative to a longitudinal axis of a plate of the device.
Figure 10:
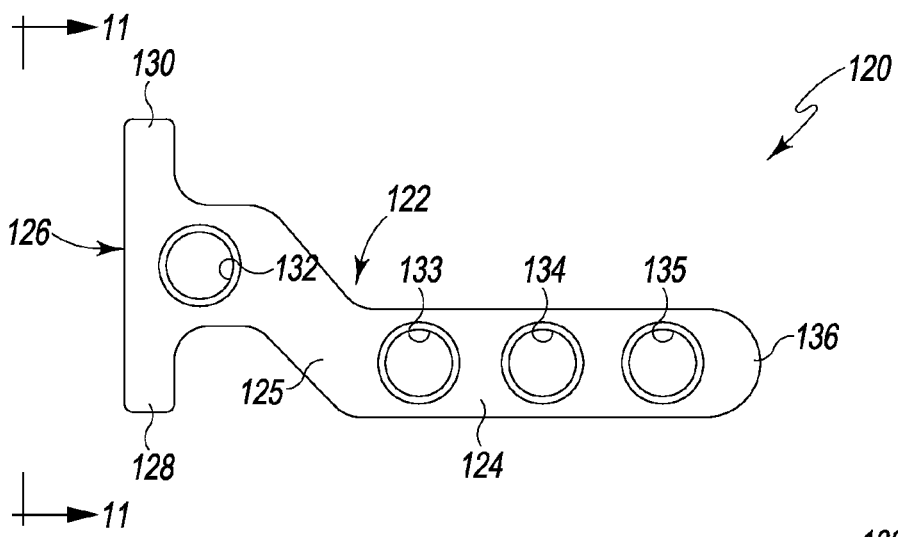
FIG. 10 is a top view of the metatarsal bone fixation device of FIG. 9.
Figure 11:
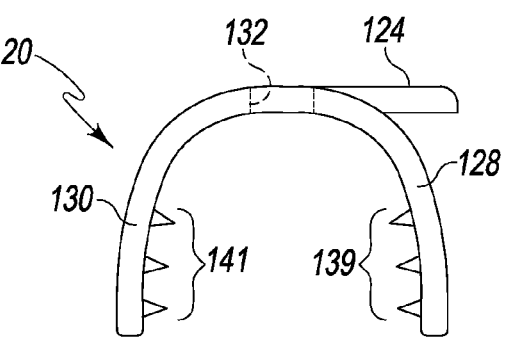
FIG. 11 is a front view of the metatarsal bone fixation device of FIG. 9 taken along line 11-11 of FIG. 10.

Referring now to FIGS. 9-11, there is depicted a metatarsal fixation device 120 fashioned in like manner to the metatarsal fixation device 20 of FIGS. 1-8 but with a modification necessary for use in cases where fixation of the epiphysis is intentionally not aligned with the original longitudinal axis of the diaphysis. The metatarsal fixation device 120 is characterized by a plate 122 having an elongated portion 124 and a clamping portion 126. The clamping portion or clamp 126 is characterized by arms 128 and 130 that extend from lateral or transverse sides of a distal end (as implanted) of the elongated portion 124. As seen in FIG. 11, the arms 128, 130 initially extend transverse to the distal end of the elongated portion 124 then curve or arch downward and away from the end of the elongated portion 124 to generally form a U shape.

The plate 122 is composed of a generally rigid but resilient, biocompatible metal that is preferably, but not necessarily, approximately 1 mm thick. The underside of the plate 122 or the surface of the plate 122 that contacts the bone surface may include a slight radius from medial to lateral to match the contour of the bone such as shown in FIG. 4A with respect to the metatarsal fixation device 20.

The elongated portion 124 of the plate 122 has an anchoring section fashioned as a plurality of threaded holes (holes 133, 134, 135) that extend along the longitudinal length of the elongated portion 124 from a proximate end 136 thereof towards a distal end thereof (i.e. the clamping portion 126). It should be appreciated that the anchoring section may include more or less threaded holes with three threaded holes being preferred. The three threaded holes 133, 134, 135 are depicted at one end of the elongated portion 124 arranged in linear orientation and evenly spaced. Other configurations, however, may be used and are contemplated.

A single threaded hole 132 is centered at the distal end of the plate 122 at the clamping portion 126. The single or isolated hole 132 is separated from the next hole 133 of the anchoring section by a crook or angled section 125 providing an appropriate distance (which in the case of a metatarsal, is approximately 10 mm). Each of the threaded holes 132, 133, 134, 135, are for receiving threaded bone screws when the device is implanted/attached in like manner as the metatarsal fixation device 20 shown in FIG. 20. The threaded holes 132, 133, 134, 135 are like the threaded hole 32 shown in FIG. 4A.

The clamping portion 126 is characterized by two arms 128, 130 that project from lateral sides of the distal end of the elongated plate 124. The arms 128, 130 project transverse from the lateral sides of the distal end of the elongated plate 124 then extend downwardly to generally form a U shape. The arm 128 includes an attachment structure 139 on an inside surface thereof. The attachment structure 139 is defined by a plurality of spikes or spike-like structures 138a, 138b, 138c that project inward from the inside surface of the arm 128. Preferably, but not necessarily, the spikes 138a, 138b, 138c are the same shape and size. In one form, the spikes 138a, 138b, 138c protrude 1 mm from the inner surface of the arm 128. It should be appreciated however, that the spikes of the attachment structure 139 may be shaped and sized differently if desired. Also, the spikes 138a, 138b, 138c are preferably, but not necessarily, evenly spaced relative to each other beginning proximate an end of the arm 128 distal the elongated plate 124. The spikes provide points of contact with the metatarsal head affording various points of fixation. The spikes 138a, 138b, 138c are shaped and sized to grasp or clamp against, affix or attach to, a lateral side of a metatarsal head. Additionally, the spikes 138a, 138b, 138c grasp, clamp or compress against a capsule or a capsule portion of the metatarsal joint which then affixes or attaches the capsule or capsule portion of the metatarsal joint to a lateral side of the metatarsal head, thereby facilitating realignment of the metatarsalsophalageal joint and respective digit.

The arm 130 includes an attachment structure 141 on an inside surface thereof in like manner as the attachment structure 139 of the arm 128. The attachment structure 141 is defined by a plurality of spikes or spike-like structures 140a, 140b, 140c that project inward from the inside surface of the arm 130. Preferably, but not necessarily, the spikes 140a, 140b, 140c are the same shape and size. In one form, the spikes 140a, 140b, 140c protrude 1 mm from the inner surface of the am 130. It should be appreciated however, that the spikes of the attachment structure 141 may be shaped and sized differently if desired. Also, the spikes 140a, 140b, 140c are preferably, but not necessarily, evenly spaced relative to each other beginning proximate an end of the arm 130 distal the elongated plate 124. The spikes provide points of contact with the metatarsal head affording various points of fixation. The spikes 140a, 140b, 140c are shaped and sized to grasp or clamp against, affix or attach to, a lateral side of a metatarsal head. Additionally, the spikes 140a, 140b, 140c grasp, clamp or compress against a capsule or a capsule portion of the metatarsal joint which then affixes or attaches the capsule or capsule portion of the metatarsal joint to a lateral side of the metatarsal head, thereby facilitating realignment of the metatarsalsophalageal joint and respective digit.

The arms 128, 130 are resilient or spring-like such that they return to their original shape after being spread, such as during implantation of the device. Particularly, the resilient arms 128, 130 are configured and shaped to compress, grasp or clamp against or attach to lateral sides of the metatarsal head under their own natural resilient force. As such, the attachment structures 139, 141 (and, particularly the spikes 138, 140 of the attachment structures 139, 141) contact, compress and grasp or clamp onto the metatarsal head with or without clamping or securing of a capsule or capsule portion, depending on whether the clamping portion 126 is used extracapsularly (with capsule securing) or intracapsularly (without capsule securing). This is the same as that illustrated in FIG. 8 for the metatarsal fixation device 20.

The crook or angled section 125 of the plate 122 provides an offset of the clamping portion 126 relative to the elongated portion 124 relative to a lateral side of the elongated portion 124. Thus, the longitudinal axis of the fixed epiphysis is offset a given amount corresponding to the amount of offset provided by the crook 125 relative to the longitudinal axis of the diaphysis. The amount of offset may vary depending on the amount of offset required. As such, plates 122 may be made with different offsets or crooks 125 to accommodate desired outcomes.

Referring now to FIGS. 12-14, there is depicted a metatarsal fixation device 220 fashioned in like manner to the metatarsal fixation device 120 of FIGS. 9-11 but with a crook or angled section 225 that projects from a lateral side of the elongated plate opposite to that of the metatarsal fixation device 120. As such, the metatarsal fixation device 220 is used in cases where fixation of the epiphysis is intentionally not aligned with the original longitudinal axis of the diaphysis. The metatarsal fixation device 220 is characterized by a plate 222 having an elongated portion 224 and a clamping portion 226. The clamping portion or clamp 226 is characterized by arms 228 and 230 that extend from lateral or transverse sides of a distal end (as implanted) of the elongated portion 224. As seen in FIG. 14, the arms 228, 230 initially extend transverse to the distal end of the elongated portion 224 then curve or arch downward and away from the end of the elongated portion 224 to generally form a U shape.

The plate 222 is composed of a generally rigid but resilient, biocompatible metal that is preferably, but not necessarily, approximately 1 mm thick. The underside of the plate 222 or the surface of the plate 222 that contacts the bone surface may include a slight radius from medial to lateral to match the contour of the bone such as shown in FIG. 4A with respect to the metatarsal fixation device 20.

The elongated portion 224 of the plate 222 has an anchoring section fashioned as a plurality of threaded holes (holes 233, 234, 235) that extend along the longitudinal length of the elongated portion 224 from a proximate end 236 thereof towards a distal end thereof (i.e. the clamping portion 226). It should be appreciated that the anchoring section may include more or less threaded holes with three threaded holes being preferred. The three threaded holes 233, 234, 235 are depicted at one end of the elongated portion 224 arranged in linear orientation and evenly spaced. Other configurations, however, may be used and are contemplated.

A single threaded hole 232 is centered at the distal end of the plate 222 at the clamping portion 226. The single or isolated hole 232 is separated from the next hole 233 of the anchoring section by a crook or angled section 225 providing an appropriate distance (which in the case of a metatarsal, is approximately 10 mm). Each of the threaded holes 232, 233, 234, 235, are for receiving threaded bone screws when the device is implanted/attached in like manner as the metatarsal fixation device 20 shown in FIG. 20. The threaded holes 232, 233, 234, 235 are like the threaded hole 32 shown in FIG. 4A.

The clamping portion 226 is characterized by two arms 228, 230 that project from lateral sides of the distal end of the elongated plate 224. The arms 228, 230 project transverse from the lateral sides of the distal end of the elongated plate 224 then extend downwardly to generally form a U shape. The arm 228 includes an attachment structure 239 on an inside surface thereof. The attachment structure 239 is defined by a plurality of spikes or spike-like structures 238a, 238b, 238c that project inward from the inside surface of the arm 228. Preferably, but not necessarily, the spikes 238a, 238b, 238c are the same shape and size. In one form, the spikes 238a, 238b, 238c protrude 1 mm from the inner surface of the arm 228. It should be appreciated however, that the spikes of the attachment structure 239 may be shaped and sized differently if desired. Also, the spikes 238a, 238b, 238c are preferably, but not necessarily, evenly spaced relative to each other beginning proximate an end of the arm 228 distal the elongated plate 224. The spikes provide points of contact with the metatarsal head affording various points of fixation. The spikes 238a, 238b, 238c are shaped and sized to grasp or clamp against, affix or attach to, a lateral side of a metatarsal head. Additionally, the spikes 238a, 238b, 238c grasp, clamp or compress against a capsule or a capsule portion of the metatarsal joint which then affixes or attaches the capsule or capsule portion of the metatarsal joint to a lateral side of the metatarsal head, thereby facilitating realignment of the metatarsalsophalageal joint and respective digit.

The arm 230 includes an attachment structure 241 on an inside surface thereof in like manner as the attachment structure 239 of the arm 228. The attachment structure 241 is defined by a plurality of spikes or spike-like structures 240a, 240b, 240c that project inward from the inside surface of the arm 230. Preferably, but not necessarily, the spikes 240a, 240b, 240c are the same shape and size. In one form, the spikes 240a, 240b, 240c protrude 1 mm from the inner surface of the am 230. It should be appreciated however, that the spikes of the attachment structure 241 may be shaped and sized differently if desired. Also, the spikes 240a, 240b, 240c are preferably, but not necessarily, evenly spaced relative to each other beginning proximate an end of the arm 230 distal the elongated plate 224. The spikes provide points of contact with the metatarsal head affording various points of fixation. The spikes 240a, 240b, 240c are shaped and sized to grasp or clamp against, affix or attach to, a lateral side of a metatarsal head. Additionally, the spikes 240a, 240b, 240c grasp, clamp or compress against a capsule or a capsule portion of the metatarsal joint which then affixes or attaches the capsule or capsule portion of the metatarsal joint to a lateral side of the metatarsal head, thereby facilitating realignment of the metatarsalsophalageal joint and respective digit.

The arms 228, 230 are resilient or spring-like such that they return to their original shape after being spread, such as during implantation of the device. Particularly, the resilient arms 228, 230 are configured and shaped to compress, grasp or clamp against or attach to lateral sides of the metatarsal head under their own natural resilient force. As such, the attachment structures 239, 241 (and, particularly the spikes 238, 240 of the attachment structures 239, 241) contact, compress and grasp or clamp onto the metatarsal head with or without clamping or securing of a capsule or capsule portion depending on whether the clamping portion 226 is used extracapsularly (with capsule securing) or intracapsularly (without capsule securing). This is the same as that illustrated in FIG. 8 for the metatarsal fixation device 20.

The crook or angled section 225 of the plate 222 provides an offset of the clamping portion 226 relative to the elongated portion 224 relative to the lateral side of the elongated portion 224 opposite to the lateral side of the offset of the metatarsal fixation device 120. Thus, the longitudinal axis of the fixed epiphysis is offset a given amount corresponding to the amount of offset provided by the crook 225 relative to the longitudinal axis of the diaphysis. The amount of offset may vary depending on the amount of offset required. As such, plates 222 may be made with different offsets or crooks 225 to accommodate desired outcomes.

Figure 15:
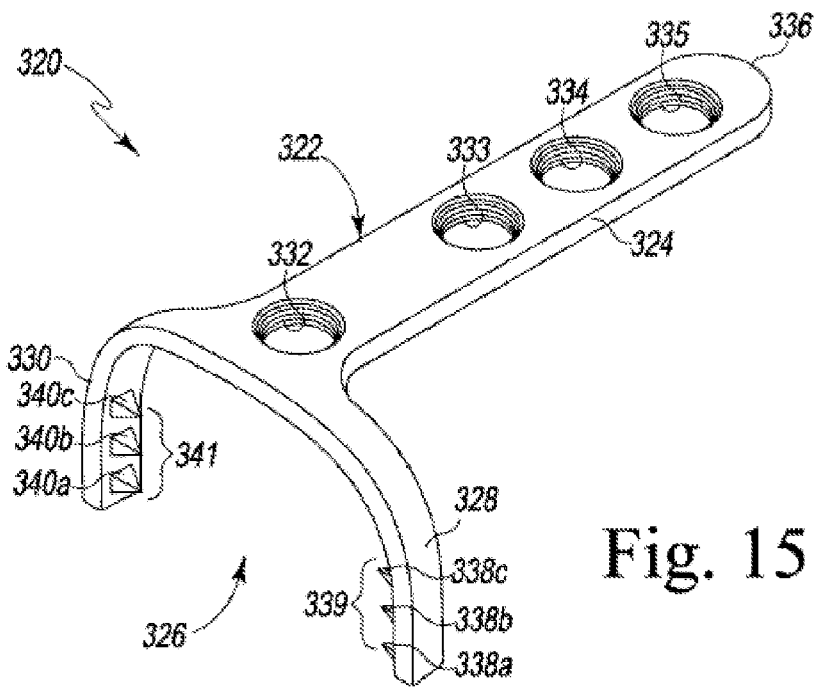
FIG. 15 is an oblique view of another embodiment of a metatarsal bone fixation device fashioned in accordance with the present principles.
Figure 16:
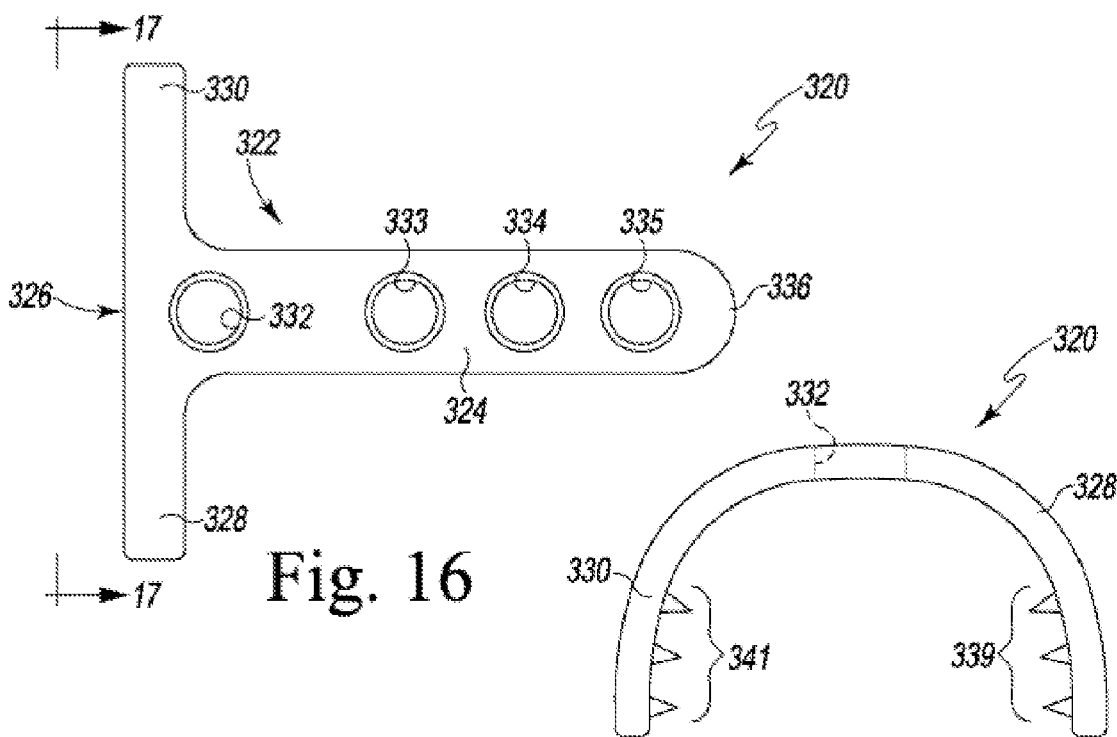
FIG. 16 is a top view of the metatarsal bone fixation device of FIG. 15.
Figure 17:
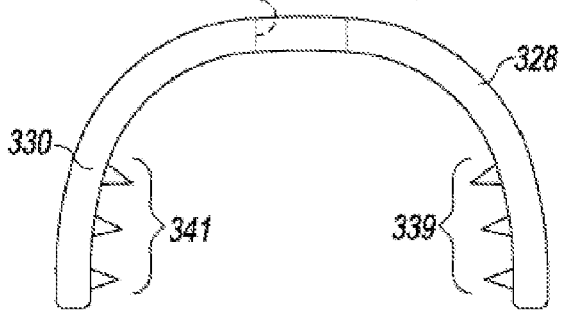
FIG. 17 is a front view of the metatarsal bone fixation device of FIG. 15 taken along line 17-17 of FIG. 16.

It should be appreciated that the metatarsal fixation devices 20, 120, and 220 may be made in various sizes in order to accommodate variations in anatomy as well as use. In the present case, the metatarsal fixation devices 20, 120, 220 may come in various sizes for the various sizes of metatarsals both with respect to an individual and in general. Variations in the length and curvature of the respective elongated portions 24, 124, 224 are contemplated as well as thickness, curvature and length of the respective arms thereof. Each arm thereof is thus sized appropriately for the particular bone. In the present metatarsal application, each arm may be approximately 2 mm wide. Referring to FIGS. 15-17, there is depicted a variation in size for a metatarsal fixation device 320, particularly in the size of the clamping portion 326 thereof in order to illustrate that the metatarsal fixation device (or other bone fixation device) may be fashioned having various dimensions. The clamping portion 326 of the bone fixation device 320 provides a U shape that is wider than the U shape of the clamping portions 26, 126, 226 of the respective metatarsal fixation devices 20, 120, 220. It should be appreciated that the various components and features of the bone fixation device 320 that are the same or similar to the various components and features of the bone fixation devices 20, 120, 220 are labeled in like manner but in the three hundreds.

Figure 18:
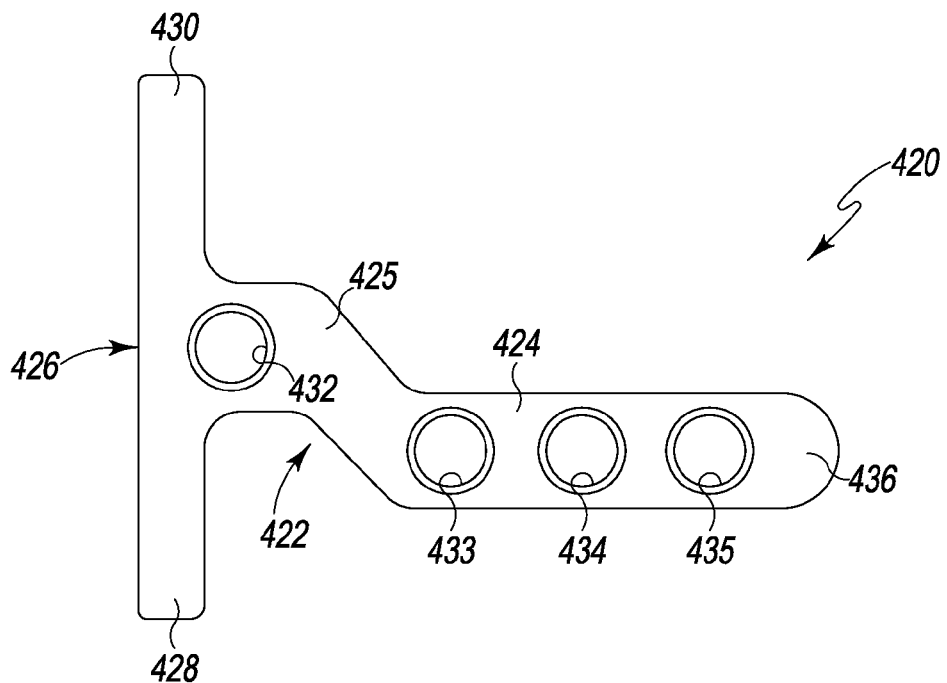
FIG. 18 is a top view of an another embodiment of a metatarsal bone fixation device fashioned in accordance with the present principles, an attachment portion of the device angled or offset relative to a longitudinal axis of a plate of the device.
Figure 19:
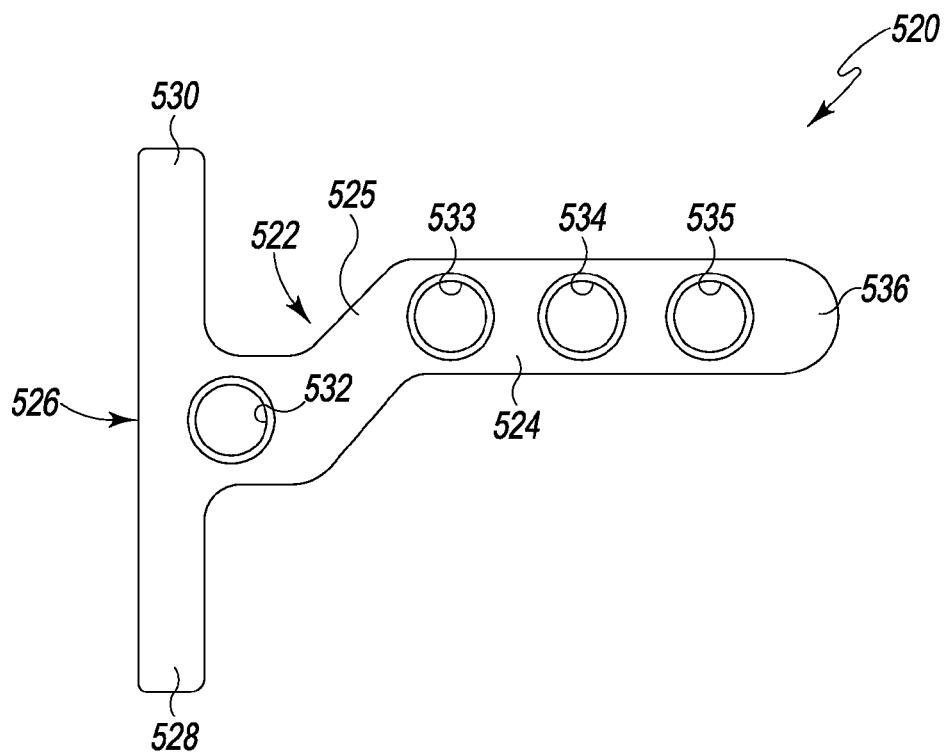
FIG. 19 is a top view of an another embodiment of a metatarsal bone fixation device fashioned in accordance with the present principles, an attachment portion of the device angled or offset relative to a longitudinal axis of a plate of the device.

FIGS. 18 and 19 provide two further metatarsal fixation devices 420 and 520 each a variation in size of the two metatarsal fixation devices 120 and 220 respectively, and particularly, a variation in size of their respective clamping portions 426, 526. It should be appreciated that the various components and features of the metatarsal fixation devices 420 and 520 that are the same or similar to the various components and features of the bone fixation devices 120 and 220 are labeled in like manner but in the four and five hundreds respectively. Of course, the bone fixation plate may also have variations in other parts not specifically shown herein such as variations in the dimensions of the elongated portion of the plate, such as length, width and hole spacing.

With reference to FIG. 20, the metatarsal fixation plate 22 is shown implanted onto a fractured metaphysis of a metatarsal and thus joining or holding together the epiphysis to the diaphysis of the fractured metatarsal. The attachment structure 39 of the arm 28 engages, contacts, grasps or clasps a portion of the epiphysis, particularly from a middle (e.g. upper) area of the epiphysis around to and extending about a lateral side thereof. The attachment structure 41 of the arm 30 engages, contacts, grasps or clasps another portion of the epiphysis, particularly from the middle area of the epiphysis around to and extending about a medial side thereof. Bone screws 990 are shown extending through the various threaded bores of the plate 22 and into the diaphysis and epiphysis. Particularly the threaded shafts 991 extend into the metatarsal bone while the heads 992 are retained on the plate 22 by the configuration of the bore holes. The arms 28, 30 are shown implanted in an intracapsular manner (i.e. under the capsule/soft tissue/ligament).

While not shown, the arms 28, 30 and the associated attachment structures 39, 41 may additionally engage, contact, grasp or clasp a portion of the capsule and/or other tissue or ligament that may have become detached, cut and/or modified such as in the case of corrections to provide lengthening or releasing the soft tissue about the metatarsal. Tightening of the capsule or soft tissue is performed by removing a section or advancing the lax capsule/soft tissue from its original attachment and reattaching. The arms 28, 30 would then be implanted in an extracapsular manner (i.e. over the capsule/soft tissue/ligament).

Figures 21, 22:
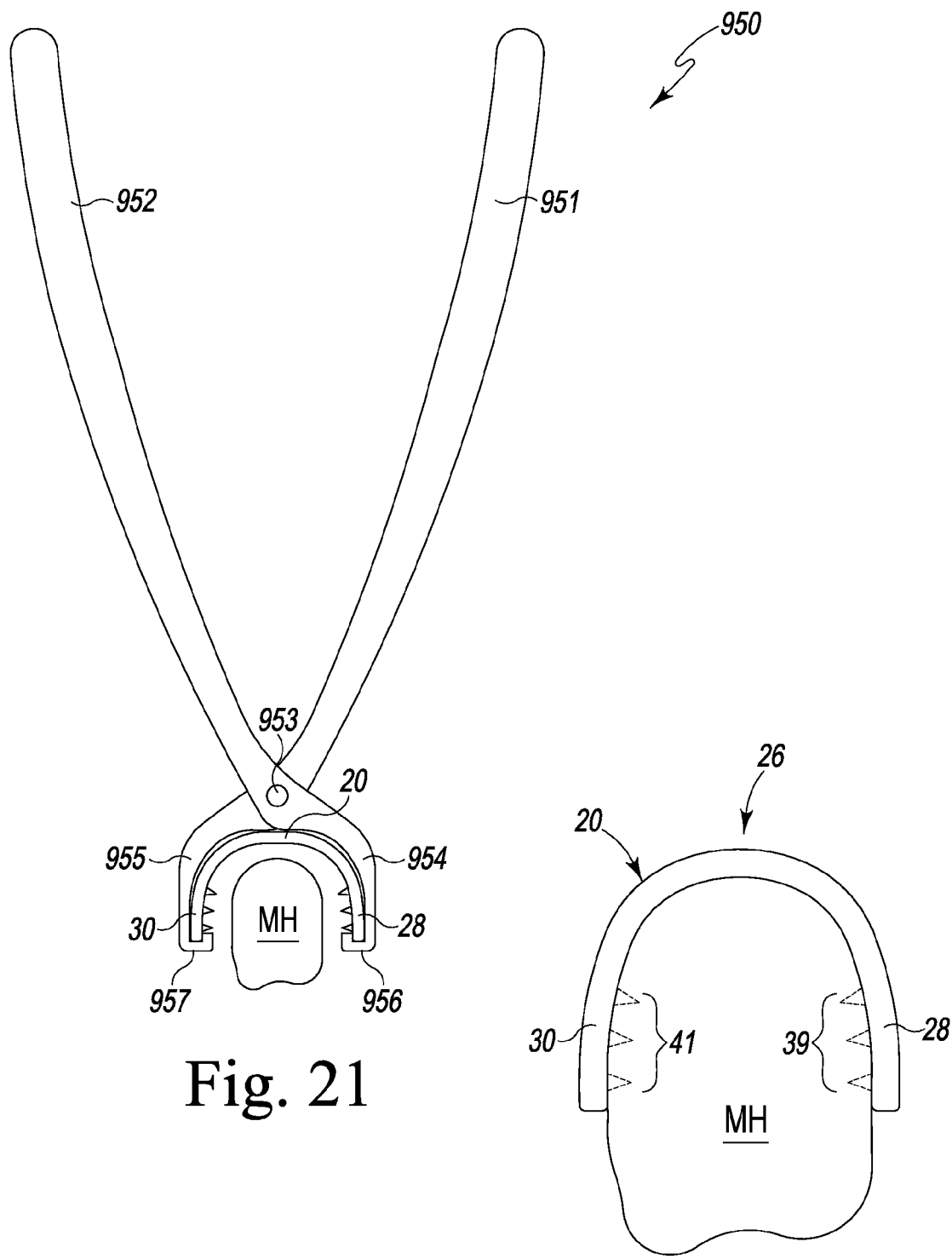
FIG. 21 is an end view of an exemplary instrument for installing any embodiment of a metatarsal bone fixation device, the installation instrument depicted expanding the arms and attachment structures of the attachment portion of the metatarsal fixation device prior to affixation of the metatarsal bone fixation device onto the metatarsal head via jaws of the installation instrument.
FIG. 22 is an enlarged end view of the metatarsal head with a metatarsal bone fixation device engaging the metatarsal head with its attachment structures.

In FIG. 21 an exemplary instrument 950 for implanting the present fixation device is shown. The instrument 950 is formed by two curved handles 951, 952 that are hinged at pivot 953. The first handle 951 has a distal portion 955 comprising a configured end 957 proximate the pivot 953 while the second handle 952 likewise has distal portion 954 having a configured end 956 proximate the pivot 953. The configured end 957 extends under and around the arm 30 in order to engage and hold the arm 30. The configured end 956 extends under and around the arm 28 in order to engage and hold the arm 28. In this manner, the configured ends 956, 957 allow the instrument or tool 950 to hold open and/or spread (bias) the arms 28, 30 for implantation. Once the clamping portion 26 is properly positioned, the tool 950 releases the arms 28, 30 to allow them to spring or bias onto the metatarsal head MH (epiphysis/capsule) as depicted in FIG. 22. Variations in the instrument 950 are contemplated. The method of expanding the arms into place by the present instrument and thus grasping the metatarsal head through release of the expansion force can also be accomplished by additional methods.

The elongated portion and the clamping portion of the present fixation device are preferably, but not necessarily, anatomically congruous to the associated metatarsal parts. As shown in FIG. 20, the plate is attached to the metatarsal diaphysis with the series of locking screws along the elongated portion, and to the metatarsal head by one locking screw and the two attachment structures of the arms. The area of the plate between the series of holes of the elongated portion and the isolated hole of the clamping portion spans the metatarsal metaphysis mending an area of osteotomy or fracture.

Some variations of the invention will occur to those skilled in the art. Without being exhaustive, variations include the use of non-locking screws and different sizes of screws. The plate size and shape may vary to match the anatomy. The angle of the arms with respect to the longitudinal portion of the plate may vary. All such variations are intended to be within the scope and spirit of the invention. Shown are exemplary embodiments only.

It should also be appreciated that although the present bone fixation device has been shown and described in particularity with respect to a metatarsal or foot bones, it is applicable to metacarpal or hand bones; those bones being very similar in anatomy.

What is claimed is:

1. A plate for fixing an osteotomy or fracture of a bone comprising:
an elongate portion defining a proximate end and a distal end, the elongate portion configured to extend along a shaft of the bone having the osteotomy or fracture;
a plurality of threaded bores disposed along the elongate portion;
a singular threaded bore disposed at the distal end of the elongate portion;
a clamping portion disposed at the distal end of the elongate portion, the clamping portion having:
a first resilient arm extending outwardly and downwardly from a lateral side of the distal end of the elongate portion;
a second resilient arm extending outwardly and downwardly from a medial side of the distal end of the elongate portion;
a first plurality of attachment structures extending outwardly from a solid inner surface of the first resilient arm; and
a second plurality of attachment structures extending outwardly from a solid inner surface of the second resilient arm; wherein the first and second resilient arms are normally biased to compress against the lateral and medial sides of a head of the bone having the osteotomy or fracture and any associated soft tissue; and
a transition section disposed between the distal end of the elongate portion and the clamping portion, the transition section angled such that the clamping portion is offset from a longitudinal axis of the elongate portion.

2. The plate of claim 1, wherein the first and second resilient arms generally form a U shape.

3. The plate of claim 1, wherein:
the first plurality of attachment structures comprise a first plurality of spikes; and
the second plurality of attachment structures comprise a second plurality of spikes.

4. The plate of claim 3, wherein:
the first plurality of spikes comprises three spikes; and
the second plurality of spikes comprises three spikes.

5. The plate of claim 4, wherein the three spikes of the first plurality of spikes and the three spikes of the second plurality of spikes are all the same size and shape.

6. The plate of claim 1,
wherein the transition section is angled such that the clamping portion is offset from the longitudinal axis of the elongate portion at a lateral side of the elongate portion.

7. The plate of claim 1,
wherein the transition section is angled such that the clamping portion is offset from the longitudinal axis of the elongate portion at a medial side of the elongate portion.

8. The plate of claim 1, wherein an under surface of the elongate portion is curved medially to laterally.

9. A plate for fixing an osteotomy or fracture of a metatarsal comprising:
an elongate portion defining a proximate end and a distal end, the elongate portion configured to extend along a metatarsal shaft of the metatarsal having the osteotomy or fracture;
a plurality of threaded bores disposed in and along the elongate portion;
a singular threaded bore disposed at the distal end of the elongate portion;
a clamping portion disposed on the distal end of the elongate portion, the clamping portion having:
a first resilient arm extending outwardly and downwardly from a lateral side of the distal end of the elongate portion;
a second resilient arm extending outwardly and downwardly from a medial side of the distal end of the elongate portion;
a first plurality of attachment structures extending outwardly from an inner surface of the first resilient arm; and
a second plurality of attachment structures extending outwardly from an inner surface of the second resilient arm; wherein
the first and second resilient arms are normally biased to compress against the lateral and medial sides of a metatarsal head of the bone having the osteotomy or fracture and any associated soft tissue; and
a transition section disposed between the distal end of the elongate portion and the clamping portion, the transition section angled such that the clamping portion is offset from a longitudinal axis of the elongate portion.

10. The plate of claim 9, wherein the first and second resilient arms generally form a U shape.

11. The plate of claim 9, wherein:
the first plurality of attachment structures comprise a first plurality of spikes; and
the second plurality of attachment structures comprise a second plurality of spikes.

12. The plate of claim 11, wherein:
the first plurality of spikes comprises three spikes; and
the second plurality of spikes comprises three spikes.

13. The plate of claim 12, wherein the three spikes of the first plurality of spikes and the three spikes of the second plurality of spikes are all the same size and shape.

14. The plate of claim 9,
wherein the transition section is angled such that the clamping portion is offset from the longitudinal axis of the elongate portion at a lateral side of the elongate portion.

15. The plate of claim 9,
wherein the transition section is angled such that the clamping portion is offset from the longitudinal axis of the elongate portion at a medial side of the elongate portion.

16. The plate of claim 9, wherein an under surface of the elongate portion is curved medially to laterally.

* * * * *